United States Patent [19]

Tsang et al.

[11] Patent Number: 5,955,588

[45] Date of Patent: Sep. 21, 1999

[54] NON-THROMBOGENIC COATING COMPOSITION AND METHODS FOR USING SAME

[75] Inventors: Ray Tsang, Salt Lake City; Shigemasa Osaki, Sandy, both of Utah

[73] Assignee: Innerdyne, Inc., Sunnyvale, Calif.

[21] Appl. No.: 09/159,276

[22] Filed: Sep. 22, 1998

Related U.S. Application Data

[60] Provisional application No. 60/068,374, Dec. 22, 1997.

[51] Int. Cl.⁶ .............................. C08B 37/10; A01N 1/00; A61M 5/32; A61L 33/00
[52] U.S. Cl. ............................... 536/21; 514/56; 523/112; 604/266; 427/2.1; 427/2.24; 427/2.25; 427/2.3
[58] Field of Search ................................... 536/21; 514/56; 523/112; 604/266; 427/2.1, 2.24, 2.25, 2.3

[56] References Cited

U.S. PATENT DOCUMENTS

| | | | |
|---|---|---|---|
| 5,338,770 | 8/1994 | Winters et al. | 523/112 |
| 5,463,010 | 10/1995 | Hu et al. | 528/25 |
| 5,541,167 | 7/1996 | Hsu et al. | 514/56 |

OTHER PUBLICATIONS

Kim et al. *Journal of Applied Polymer Science* 1994, 54(12), 1863–72.

*Primary Examiner*—Kathleen K. Fonda
*Attorney, Agent, or Firm*—Townsend and Townsend and Crew LLP

[57] ABSTRACT

The present invention provides an anti-thrombogenic coating composition for blood-contacting surfaces. The coating comprises a covalent complex of from 1 to 30 hydrophobic silyl moieties of Formula I:

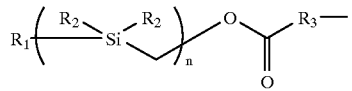

wherein $R_1$ is a $C_{1-8}$ alkyl or $C_{6-32}$ aryl group, each $R_2$ is independently selected from the group consisting of $C_{1-8}$ alkyl and $C_{6-32}$ aryl, $R_3$ is N or O, and n is a number from 1 to 10, directly bound to a heparin molecule via covalent bonding.

28 Claims, No Drawings

NON-THROMBOGENIC COATING COMPOSITION AND METHODS FOR USING SAME

This application is a continuation of, and claims the benefit of priority from (provisional) application No. 60/068,374, filed on Dec. 22, 1997, the full disclosure of which is incorporated herein by reference.

BACKGROUND OF THE INVENTION

The use of disposable medical devices derived from synthetic and natural polymers has grown in recent years. These devices include monitoring tubes, artificial organs, catheters, blood filters, oxygenators, tubing sets and other devices that come into direct contact with blood during surgical or other medical treatment procedures. Recently, certain synthetic plastics have come into common use due to their desirable properties. These plastic materials have increased the ease of device manufacturing and are frequently the preferred materials for certain applications in prosthetic device technology.

One common property shared by all medical grade plastics is the possibility of the formation of thrombus on the surface when the plastic comes into direct contact with blood. The formation of thrombus or a clot creates the possibility of a number of serious complications. These include blood flow stoppage, pulmonary embolism, cerebral thrombosis or myocardial infarction. Traditionally, clinicians decrease the risk of thrombus by the administration of anticoagulants such as heparin, coumadin or other pharmacological agents. However, administration of these anticoagulants can be undesirable in some instances, because the anticoagulants may give rise to bleeding complications and because their anticoagulant effects are not easily reversed should bleeding complications such as gastrointestinal bleeding, occur.

Heparin is one well known systemic anticoagulant. This sulfated amino glycan polysaccharide of variable molecular weight is known to increase the inactivation rate of serum proteases such as thrombin and Factor Xa in conjunction with the inhibitor antithrombin III. Consequently, in the presence of heparin, the blood is less likely to form a thrombus and thereby avoid serious life threatening sequela. A review of the clinical biochemistry of heparin and its anticoagulation effects can be found in HEPARIN: CHEMICAL AND BIOLOGICAL PROPERTIES, CLINICAL APPLICATIONS (1989) edited by D. Lane et al., CRC Press, Inc., Boca Raton, Fla.

Due to the side effects resulting from direct systemic administration of sodium heparin, some researchers have sought to develop means for coating heparin onto those surfaces of medical devices that are intended to come into direct contact with blood. One example of a heparin coating is proposed in V. Gott, Science 142:1297 (1993). Gott proposes a coating for a graphite plastic surface which involves the cationic surfactant, benzalkonium chloride, complexed to the polyanion heparin. This ionic complex of cationic surfactant and heparin adheres to the surface of the plastic by virtue of the hydrophobic nature of the surfactant molecule and its attraction for the graphite surface.

Other approaches for coating heparin on a surface were proposed in U.S. Pat. Nos. 3,810,781 and 4,118,485 which relate to the treatment of heparin-coated surfaces with dialdehyde in order to crosslink the heparin molecules. U.S. Pat. No. 4,265,927 proposes treating a charged surface with heparin by contacting the surface with a colloidal aqueous solution of a complex compound of heparin and a cationic surfactant. The use of the dialdehyde purportedly affords a more stabilized heparin coating. However, the crosslinking that occurs in the heparin results in a decrease in the anti-thrombogenic activity of the heparin. The decrease in anti-thrombogenic activity observed by crosslinked heparin coatings is a common result of attempts to chemically modify heparin.

A number of heparin coatings based upon the formation of an ionic complex with sodium heparin or a heparin derivative are commercially available. Examples of such coatings include BENZALKONIUM HEPARIN® from Polyscience, Inc, TDMAC® heparin from Polyscience, Inc., and DUROFLOW II® from Baxter Biocompatible Technologies. These coatings are subject to leaching of the heparin due to the ionic nature of blood plasma. More specifically, heparin is lost from the surface as the cationic surfactant exchanges for other counterions present in the blood, such as sodium, potassium, and others.

Other heparin coatings have been developed which utilize alkylammonium salts as the cationic portion of the complex. For example, U.S. Pat. No. 4,046,725 proposes a polyurethane copolymer for use in the production of articles which contact the blood. The copolymer contains quaternary ammonium groups to which the heparin coating binds. U.S. Pat. No. 5,391,580 proposes a poly(sulfone-alpha-olefin) composite article for use in blood oxygenation. The article includes a polypropylene tube, and a polysulfone perm-selective homogeneous layer directly adhered to the polypropylene tube. Heparin is covalently linked to the polysulfone perm-selective layer.

There remains a need in the art for heparin coating compositions which can be applied to blood-contacting surfaces of medical devices. There further remains a need in the art for heparin coating compositions which do not lose their anti-thrombogenic effects over time. There remains a need in the art for heparin coating compositions which can be produced in a cost-effective and commercially feasible manner and which can be applied to blood-contacting surfaces of medical devices in a commercially feasible manner.

SUMMARY OF THE INVENTION

The present invention relates to new anti-thrombogenic coating compositions. According to the compositions of the present invention, hydrophobic moieties are covalently bound to a heparin molecule to form a covalent complex.

As a first aspect, the present invention provides an anti-thrombogenic coating composition for blood-contacting surfaces. The coating comprises a covalent complex of from 1 to 30 hydrophobic silyl moieties of Formula I:

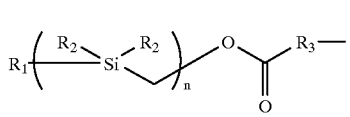

wherein $R_1$ is an $C_{1-8}$ alkyl or $C_{6-32}$ aryl group, each $R_2$ is independently selected from the group consisting of $C_{1-8}$ alkyl and $C_{6-32}$ aryl, $R_3$ is N or O, and n is a number from 1 to 10, directly bound to a heparin molecule via covalent bonding.

As a second aspect, the present invention provides a non-thrombogenic medical device comprising surfaces for contacting blood. The blood-contacting surfaces have coated thereon an anti-thrombogenic coating composition. The anti-thrombogenic coating composition comprises a covalent complex of from 1 to 30 hydrophobic silyl moieties of Formula I directly bound to a heparin molecule via covalent bonding.

As a third aspect, the present invention provides a method for rendering blood-contacting surfaces of a medical device non-thrombogenic. The method comprises coating the surfaces with an anti-thrombogenic coating composition. The composition comprises a covalent complex of from 1 to 30 hydrophobic silyl moieties of Formula I directly bound to a heparin molecule via covalent bonding.

As a fourth aspect, the present invention provides a covalent complex of Formula II:

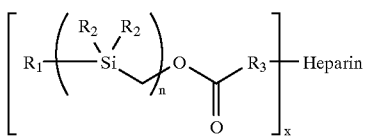

wherein $R_1$ is an $C_{1-8}$ alkyl or $C_{6-32}$ aryl group, each $R_2$ is independently selected from the group consisting of $C_{1-8}$ alkyl and $C_{6-32}$ aryl, $R_3$ is N or O, n is a number from 1 to 10, and x is a number from 1 to 30.

These and other aspects of the present invention are described further in the description of the preferred embodiment and examples of the invention which follow.

DESCRIPTION OF THE PREFERRED EMBODIMENT

Unless otherwise defined, all technical and scientific terms employed herein have their conventional meaning in the art. As used herein, the following terms have the means ascribed to them.

"Alkyl" refers to linear branched or cyclic, saturated or unsaturated $C_{1-8}$ hydrocarbons such as methyl, ethyl, ethenyl, propyl, propenyl, iso-propyl, butyl, iso-butyl, t-butyl, pentyl, cyclopentyl, hexyl, cyclohexyl, octyl, and the like.

"Aryl" refers to unsaturated $C_{6-32}$ hydrocarbon rings which may be substituted from 1–5 times with alkyl, halo, or other aryl groups. Aryl also includes bicyclic aryl groups. Specific examples of aryl groups include but are not limited to phenyl, benzyl, dimethyl phenyl, tolyl, methyl benzyl, dimethyl benzyl, trimethyl phenyl, ethyl phenyl, ethyl benzyl, and the like.

The heparin coating compositions of the present invention comprise a covalent complex of one or more hydrophobic silyl moieties with heparin. Heparin is a mixture of variably sulfated polysaccharide chains composed of repeating units of D-glucosamine and either L-iduronic or D-glucuronic acids.

Any suitable form of heparin may be employed in the reaction. Several salts of heparin and heparin derivatives are known in the art. For example, conventional salts of heparin include sodium heparin, calcium heparin, magnesium heparin, and potassium heparin. Heparin derivatives include, but are not limited to ammonium heparin, benzalkonium heparin, and the like. Sodium heparin is one preferred form of heparin for preparing the covalent complexes according to the present invention. For the sake of simplicity, the term "heparin molecule" refers to any of known forms of heparin including all salts and derivatives of heparin.

The silyl moiety is represented by the general Formula I:

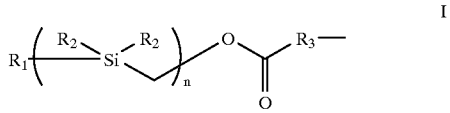

wherein $R_1$ is an $C_{1-8}$ alkyl or $C_{6-32}$ aryl group, each $R_2$ is independently selected from the group consisting of $C_{1-8}$ alkyl and $C_{6-32}$ aryl, $R_3$ is N or O, and n is a number from 1 to 10. As will be apparent to those skilled in the art, $R_3$ is an N or O atom on the heparin molecule, and the unoccupied bond from $R_3$ signifies the attachment of the silyl moiety to the heparin molecule. Thus, the hydrophobic silyl moiety is capable of attachment to the heparin molecule at either an O atom of an alcohol (i.e., hydroxyl) or a N atom of an amine.

Heparin comprises many repeating units containing amine and hydroxyl functional groups which can be the site for attachment of the hydrophobic silyl moiety to the heparin molecule. Accordingly, one embodiment of the present invention contemplates the attachment of more than 1 hydrophobic silyl moiety to a single heparin molecule. As many as 30 hydrophobic silyl moieties of Formula I or more, and as few as 1 hydrophobic silyl moiety may be attached to a single heparin molecule to achieve the covalent complex employed in the heparin coating compositions of the present invention. In one embodiment of the present invention, between 2 and 25 hydrophobic silyl moieties are attached to a single heparin molecule. In one embodiment, between 5 and 20 hydrophobic silyl moieties are attached to a single heparin molecule. In one embodiment, between 7 and 15 hydrophobic silyl moieties are attached to a single heparin molecule. In one preferred embodiment, 7 or 8 hydrophobic silyl moieties are attached to a single heparin molecule. In another preferred embodiment 12 hydrophobic silyl moieties are attached to a single heparin molecule.

In those embodiments wherein more than one hydrophobic silyl moiety is attached to a single heparin molecule, the hydrophobic silyl moieties may be attached either through the amine of heparin (e.g., where $R_3$ is N) or through the hydroxyl group of heparin (e.g., wherein $R_3$ is O). In other words, some of they hydrophobic silyl moieties may be attached to the heparin molecule via bonding at the amine groups of heparin, while other hydrophobic silyl moieties are attached to the heparin molecule via bonding at the hydroxyl groups of heparin. It is also possible for all of the hydrophobic silyl moieties to be consistently attached to heparin via one or the other of the amine (e.g., $R_3$ in all hydrophobic silyl moieties is N) or the alcohol (e.g., $R_3$ in all hydrophobic silyl moieties is O).

The bonds between the hydrophobic silyl moieties and the heparin molecule which effect the attachment of the moieties to the molecule are covalent bonds. Thus, the coating compositions of the present invention do not rely upon ionic interactions between heparin and the hydrophobic moiety. Rather, the hydrophobic moieties are bonded to the heparin molecule by covalent bonding through either the amine or hydroxyl groups (or possibly a combination of both amine and hydroxyl groups when two or more hydrophobic silyl moieties are attached a single heparin molecule). Because the hydrophobic silyl moiety is bound to the heparin molecule through covalent bonding, the present invention overcomes one weakness of conventionally known heparin coatings. Specifically, the problem of heparin leaching from the coating as a result of the breaking of the ionic bond between heparin and the group which attaches heparin to the surface is overcome by avoiding reliance upon ionic bonding interactions between heparin and the binding group. In the present invention, the covalent bonds between the hydrophobic silyl moieties and the heparin molecule in the coating composition are not disrupted by the presence of ionic species in the blood with which the coated surface will come into contact. The data demonstrate that this process of covalent modification also does not lead to detrimental loss of heparin activity as monitored by a Factor Xa/Antithrombin III chromogenic substrate assay on the surface of target substrates.

The covalent complex according to the present invention can be prepared according to the following Scheme 1.

dimethyl formamide (DMF), at a temperature of above about 120° C., and preferably about 135° C. for between 12 and 24 hours. The product of this reaction is then reacted with sodium methoxide (NaOMe) in methanol (MeOH) under reflux for about 2 hours to achieve the second intermediate.

The second intermediate is converted to the last intermediate, $R_1(Si(R_2)_2CH_2)_nCO_2N(COCH_2)_2$, by a two-step reaction process. In the first step, the second intermediate is reacted with triphosgene and sodium carbonate in methylene chloride at a temperature of less than 10° C., and preferably about 0° C. The product of this reaction is reacted with N-hydroxysuccinimide and triethylamine ($Et_3N$) in

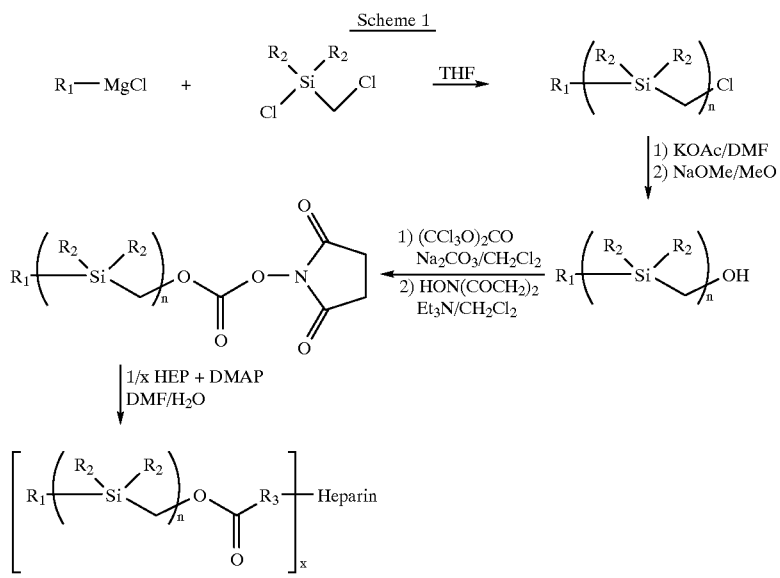

Scheme 1 wherein $R_1$ is an $C_{1-8}$ alkyl or $C_{6-32}$ aryl group, each $R_2$ is independently selected from the group consisting of $C_{1-8}$ alkyl and $C_{6-32}$ aryl, $R_3$ is N or O, n is a number from 1 to 10, and x is a number from 1 to 30.

Generally, the first intermediate, $R_1(Si(R_2)_2CH_2)_nCl$ wherein n is 1, is produced by reacting an alkyl or aryl magnesium chloride with a chloro(chloromethyl)-dialkyl silane or chloro(chloromethyl)diaryl silane in the presence of tetrahydrofuran (THF). The alkyl or aryl magnesium chlorides used as starting materials are commercially available, and include, for example benzyl magnesium chloride. The chloro(chloromethyl)dialkyl silane or chloro (chloromethyl)diaryl silanes are also commercially available and include, for example chloro(chloromethyl)dimethyl silane. The reaction is exothermic, and is typically conducted at temperatures of about 10° C. or less. The reaction is carried out for a sufficient period of time to yield about 80–90% product. Typically the reaction is conducted over a period of from about 2 to about 24 hours.

First intermediates wherein n is 2 or higher can be produced using a Grignard Reaction involving the reaction of the first intermediate wherein n is 1 with $ClSi(R_2)_2CH_2Cl$. This Grignard reaction can be repeated any number of times to achieve the desired value for n in the first intermediate. The reaction is carried out in the presence of a catalytic amount of iodine and THF.

The first intermediate (wherein n is 1–10) is converted to the second intermediate, $R_1(Si(R_2)_2CH_2)_nOH$, by reacting the first intermediate with potassium acetate (KOAc) in methylene chloride at a temperature of less than 10° C., and preferably about 0° C.

The final intermediate is covalently conjugated to heparin by reacting heparin with the final intermediate in a suitable solvent (e.g., water/dimethyl formamide) at a pH of about 8.0 to 9.0, and preferably about 8.5. The pH of the reaction is controlled by the addition of base such as sodium hydroxide, as needed.

Using these general methods, the covalent complexes of the present invention can be produced. The covalent complexes have the general Formula II:

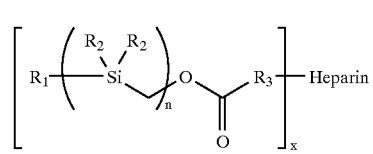

II wherein $R_1$ is an $C_{1-8}$ alkyl or $C_{6-32}$ aryl group, each $R_2$ is independently selected from the group consisting of $C_{1-8}$ alkyl and $C_{6-32}$ aryl, $R_3$ is N or O, n is a number from 1 to 10, and x is a number from 1 to 30.

Preferred complexes include those complexes wherein $R_1$ of the hydrophobic silyl moiety is aryl. In one preferred embodiment, $R_1$ is benzyl. In one preferred embodiment, each $R_2$ is alkyl. In one particularly preferred embodiment, each $R_2$ is selected from the group consisting of methyl, ethyl, propyl, and isopropyl, particularly methyl. In one preferred embodiment, n is a number from 2 to 3.

Specific examples of covalent complexes according to the present invention include but are not limited to [benzyl-bis(dimethylsilylmethyl)]-(N-heparinyl)-carbamate, [benzyl-tris(dimethylsilylmethyl)]-(N-heparinyl)-carbamate, and dodecyl[benzyl-bis(dimethylsilylmethyl)]-(N-heparinyl)-carbamate. Although these three specific covalent complexes are examples of currently preferred covalent complexes having the general Formula II above, other specific examples of such complexes will be apparent to those skilled in the art and are contemplated by the instant invention.

The coatings of the present invention comprise the covalent complexes described above. In addition to the covalent complex, the coating composition may also include one or more solvents which facilitate the processes of applying the composition to the surface. Suitable solvents will be those which at least partially solubilize the covalent complex and which do not interfere with the anti-thrombogenic activity of heparin. Examples of solvents which may be employed in the coating compositions of the present invention include but are not limited to aqueous solvents, alcohols, nitriles, amides, esters, ketones, ethers, and the like. "Aqueous" with reference to solutions or solvents refers to solutions or solvents which consist primarily of water, normally greater than 90 weight percent water, and can be essentially pure water in certain circumstances. For example, an aqueous solution or solvent can be distilled water, tap water, or the like. However, an aqueous solution or solvent can include water having substances such as pH buffers, pH adjusters, organic and inorganic salts, alcohols (e.g., ethanol), sugars, amino acids, or surfactants incorporated therein. The aqueous solution or solvent may also be a mixture of water and minor amounts of one or more cosolvents, including agronomically suitable organic cosolvents, which are miscible therewith, or may form an emulsion therewith. Examples of suitable alcohol solvents include but are not limited to methanol, ethanol, propanol, isopropanol, hexanol, as well as glycols such as ethylene glycol, and the like. Examples of suitable nitriles include acetonitrile, propionitrile, butyronitrile, benzonitrile, and the like. Examples of suitable amides include formamide, N,N-dimethylformamide, N,N-dimethylacetamide, and the like. Examples of suitable esters include methyl acetate, ethyl acetate, and the like. Examples of suitable ketones include acetone, methyl ethyl ketone, diethyl ketone, and the like. Examples of suitable ethers include diethyl ether, tetrahydrofuran, dioxane, dimethoxyethane, and the like. Any two or more of any of the foregoing solvents may be utilized in the coating composition as well. Currently preferred solvents include water, particularly distilled water, isopropanol, acetonitrile, and combinations of any two or more of these solvents.

In one preferred embodiment, the covalent complex is solubilized in solvent to achieve a concentration of between about 0.01 and about 10 percent by weight, preferably between about 0.1 and about 1 percent, and more preferably about 0.125 percent.

In addition to the foregoing solvents, the heparin coating compositions of the present invention may also include therein various conventional additives. Examples of additives which may be incorporated into the compositions of the present invention include but are not limited to benzalkonium, 4-dimethylaminopyridinium, tetrabutylammonium halides, and the like.

The coating composition may be coated onto any of a wide variety of surface materials to provide anti-thrombogenic effects when the coated surface is contacted with blood. Suitable surfaces which may be coated with the coating composition of the present invention include any surface which has an affinity or attraction to the hydrophobic silyl moiety. Such surfaces are typically hydrophobic surfaces. Examples of suitable surfaces include but are not limited to hydrophobic polymers such as polycarbonate, polyester, polypropylene, polyethylene, polystyrene, polytetrafluoroethylene, polyvinyl chloride, polyamide, polyacrylate, polyurethane, polyvinyl alcohol, and copolymers of any two or more of the foregoing; siloxanes such as 2,4,6,8-tetramethylcyclotetrasiloxane; natural and artificial rubbers; glass; and metals including stainless steal and graphite.

The heparin coating composition can be applied to the surface to render the blood-contacting surface non-thrombogenic. Any suitable method for applying the coating composition to the surface may be employed. One suitable method for applying the coating composition to the blood-contacting surface to be treated is by dipping the blood-contacting surface into the coating composition containing the covalent complex of the present invention. A liquid coating composition containing the covalent complex of the present invention may be prepared using any of the solvents described above. The surface is dipped or immersed into a bath of the coating composition. Typically, the dipping process is carried out at elevated temperatures, such as between about 30° C. and about 80° C. for a period of between about 5 and about 20 minutes, preferably about 10 minutes. Thereafter, the surface is allowed to remain in contact with the coating composition containing the covalent complex for a period of between about 15–60 minutes, preferably about 20 minutes, at room temperature.

Another method which may be employed for coating or applying the heparin coating compositions of the present invention on to blood-contacting surfaces includes a pumping or spraying processes. According to the pumping process, the coating solution having a concentration of between 0.05 and about 5 percent (w/v) is pumped through the device where the blood contact will occur for 30 minutes. Thereafter the excess coating materials is washed out with water or saline. The blood contacting surface can be coated by the material of the current invention simply by spraying with the above-mentioned coating solution as well. The coated surface is typically washed with water before drying.

Following coating of the composition onto the surface, the surface is typically washed with water or saline prior to drying. Advantageously, the foregoing methods for applying the coating composition to a surface are relatively quick, commercially feasible and cost-effective.

The hydrophobic interactions between the hydrophobic surfaces to be coated and the hydrophobic silyl moieties of the covalent complex form the bond between the covalent complex and the surface. This hydrophobic interaction is sufficiently strong so as to provide a stable bond between the covalent complex and the surface. The present inventors have now discovered a method for binding heparin to a surface by using hydrophobic binding interactions which provide certain advantages over the method relied upon in previous coating technologies. The presence of ionic species in blood does not disrupt the hydrophobic interaction between the covalent complex of the present invention and the surface.

The coating compositions of the present invention can be applied to the blood-contacting surfaces of any of a wide variety of medical devices to provide a non-thrombogenic medical device. Examples of specific medical devices which may be advantageously treated with the coating compositions of the present invention include but are not limited to oxygenators, oxygenator circuits, heart-lung bypass circuits, blood gas exchange devices, blood filters, artificial blood vessels, artificial valves, prosthetics, stents, catheters, heat exchangers, and hypodermic needles. Other examples of medical devices which would benefit from the application of the non-thrombogenic coating compositions of the present invention will be readily apparent to those skilled in the art of surgical and medical procedures and are therefore contemplated by the instant invention.

The following examples are provided to illustrate the present invention, and should not be construed as limiting thereof. In these examples, "ml" means milliliter; "L" means liter, "mg" means milligrams, "g" means grams, "mol" means moles, "M" means molar concentration, "Me" means methyl; "Bn" means benzyl, "nBu$_4$NI" means tetrabutylammonium iodide, "° C." means degrees Centigrade. All percentages are in percent by weight unless otherwise indicated.

EXAMPLE 1

This example demonstrates the method for preparing the covalent complexes of the present invention.

Synthesis of Benzyl(chloromethyl)dimethylsilane

In a 2 L 3-necked flask equipped with a nitrogen inlet, a 500 ml dropping funnel and a thermometer, was placed 500 ml of tetrahydrofuran. Chloro(chloromethyl)-dimethylsilane (100 ml, 0.744 mol) was added by syringe and the colorless solution cooled to 0° C. in an ice/acetone bath. Then benzylmagnesium chloride (2.0 M solution, 400 ml, 0.8 mol) was transferred to the dropping funnel by syringe and added dropwise over 2 hours. A slightly exothermic reaction was observed and the temperature was maintained below 10° C. After addition of the chloro(chloromethyl)dimethylsilane was complete, the ice bath was allowed to warm up to room temperature without heating, and the reaction mixture was stirred overnight. Thereafter hexane (300 ml) was added and the reaction mixture was worked up by dropwise addition of saturated aqueous ammonium chloride (300 ml) and transferred to a 2 L separatory funnel with additional hexane (300 ml). After partitioning, the organic layer was washed with saturated aqueous ammonium chloride (200 ml) and saturated aqueous sodium chloride (200 ml). The combined aqueous layers were backwashed with hexane (2×500 ml). The combined organic layers were dried over magnesium sulfate, evaporated on the rotovap, and finally evaporated with an oil pump to give a colorless oil 162.0 g (109.5% yield). A quantitative yield was assumed with a purity of the crude product as 91.3%.

Grignard Reaction of Bn(SiMe$_2$CH$_2$)$_n$Cl and ClSiMe$_2$CH$_2$Cl to give Bn(SiMe$_2$CH$_2$)$_{n+1}$Cl In a 500 ml 3-necked flask equipped with a condenser-nitrogen inlet, a septum and a thermometer, was placed magnesium powder (7.5 g, 0.31 mol), a catalytic amount of iodine and tetrahydrofuran (100 ml). The brown mixture was heated to reflux briefly with a heat gun until the color of iodine disappeared. Bn(SiMe$_2$CH$_2$)$_n$Cl (0.2 mol) was added by syringe and washed down with the tetrahydrofuran (2×25 ml). The reaction was initiated with a heat gun. An exothermic reaction was observed and the reaction flask was placed in a water bath until the exothermic reaction subsided. The resulting grey mixture was heated to reflux for 24 hours. The reagent was then cooled to room temperature and cannulated into a pressure filter funnel where it was added directly into another 500 ml round bottom flask in which was placed a solution of ClSiMe$_2$CH$_2$Cl (27.0 ml, 0.2 mol) in tetrahydrofuran (50 ml) at room temperature. The magnesium residue was washed down with tetrahydrofuran (2×25 ml). The reaction mixture was heated to reflux overnight. The resulting grey suspension was worked up by addition of saturated aqueous sodium bicarbonate (50 ml) and transferred to a 500 ml separatory funnel with hexane (200 ml). After partition, the organic layer was washed with saturated aqueous sodium bicarbonate (50 ml) and saturated aqueous sodium chloride (50 ml). Then the combined aqueous layers were back-washed with hexane (2×100 ml). The combined organic layers were dried over magnesium sulfate, evaporated on the rotovap, and finally evaporated on the oil pump to give an amber oil, which can be purified by distillation to give a colorless oil. Yield is approximately 80 percent.

Conversion of Bn(SiMe$_2$CH$_2$)$_n$Cl to Bn(SiMe$_2$CH$_2$)$_n$OH

Bn(SiMe$_2$CH$_2$)$_n$Cl (0.16 mol) was dissolved in dimethylformamide (300 ml) in a 1 L 3-necked flask. Potassium acetate (50 g, 0.5 mol) was added followed by nBu$_4$NI (4.0 g, 0.01 mol) and the reaction mixture was stirred in a 135° C. oil bath for 24 hours. The reaction mixture was worked up by cooling to room temperature, transferred to a 1 L separatory funnel with hexane (500 ml), and washed with saturated aqueous sodium chloride (3×100 ml). The combined aqueous layers were back-washed with hexane (3×300 ml). The combined organic layers dried over magnesium sulfate, and evaporated on the rotovap to give an amber oil. The oil was dissolved in methanol (400 ml). Then a generous amount of freshly prepared sodium methoxide was added to adjust the pH to >10 and the reaction mixture was heated to reflux for 2 hours. The reaction mixture was worked up by neutralizing with acetic acid (AcOH), and evaporated to dryness. The dried mixture was chromatographed with silica gel in a 6.5×100 cm (height of silica 40 cm) flash column and eluted with 0–30% ethylacetate/hexane [Rf (tlc with silica gel 60 F$_{254}$ on Al plates, eluted with 20% ethylacetate/hexane and observed as a darkened spot under UV lamp) of product=0.1] to give the desired product as a slightly yellow oil. The yield is approximately 80 percent.

Conversion of Bn(SiMe$_2$CH$_2$)$_n$OH to Bn(SiMe$_2$CH$_2$)$_n$OCO$_2$N(COCH$_2$)$_2$ Triphosgene (60 g, 0.2 mol) was dissolved in methylene chloride (200 ml) and stirred at 0° C. under nitrogen in a 1 L 3-necked flask equipped with thermometer, dropping funnel and nitrogen inlet. Sodium carbonate (65 g, 0.6 mol) was added followed by Bn(SiMe$_2$CH$_2$)$_n$OH (0.13 mol dissolved in 200 ml methylene chloride) dropwise over 30 minutes. Thereafter, the ice/acetone bath was allowed to warm to room temperature without addition of heat. The reaction mixture was allowed to stir overnight and worked up the next morning by filtering through a sintered glass funnel, which was washed down with toluene (PhCH$_3$) (200 ml). Thereafter the filtrate was evaporated on the rotovap to give a colorless oil, which was dissolved in methylene chloride and stirred in an ice bath under nitrogen. N-Hydroxysuccinimide (30 g, 0.26 mol) was added, followed by dropwise addition of triethylamine (Et$_3$N) (40 ml, 0.28 mol) over 15 minutes. The resulting cloudy mixture was stirred at room temperature for 1 hour. The reaction mixture was then worked up by diluting with hexane (600 ml), washed with saturated aqueous ammonium chloride (3×100 ml), and the combined aqueous phases backwashed with hexane (2×200 ml). The combined organic phases were dried over magnesium sulfate and evaporated to dryness on the rotovap to give an amber oil. The oil was chromatographed with silica gel in a 6.5×100 cm (height of silica 40 cm) flash column and eluted with 20–50% ethyl acetate/ hexane [Rf (tlc with silica gel 60 $F_{254}$ on Al plates, eluted with 20% ethylacetate/hexane and observed as a darkened spot under UV lamp) of product=0.1] to give an amber syrup. The yield is approximately 70 percent.

Conlugation of Heparin with $Bn(SiMe_2CH_2)_nOCO_2N(COCH_2)_2$

Heparin (ammonium free, average molecular weight 10,000; 100 g, 10 mmol) was dissolved in 500 ml of water in a 4000 ml beaker with stirring. DMF (400 ml) was added followed by DMAP (5.0 g, 40 mmol) and the pH was monitored by a 702 SM Titrino with program set at: end pont=8.50, max flow rate=1 ml/min., min. flow rate=10 $\mu$l/min., pause time=60 sec., stop criteria=time (inf.) and connected to a reservoir of 1 M sodium hydroxide. $Bn(SiMe_2CH_2)_nOCO_2N(COCH_2)_2$ (10× mmol) in DMF (100 ml) was added and the pH began to drop. The program was started as soon as the pH dropped to just below 8.5. The resulting milky mixture was allowed to stir at room temperature while the pH of the reaction mixture was maintained at 8.5 by Titrino by automateic addition of 1M sodium hydroxide as necessary. The amount of 1 M sodium hydroxide used (in ml) was plotted against reaction time (in hours) as the reaction profile. The reaction mixture was worked up, when the reaction profile begins to flatten out, by trituration with acetone (2 l) and the white suspension is filtered through a sintered glass funnel to give a white solid residue, which was contaminated with DMF and some of the residual N-hydroxy-succinimide. This crude material can be purified by soxhlet extraction with acetone overnight to give a white powder. The yields are gernally in the high 90's.

Procedure for Coating the Complexes onto the Surface

The complex is completely dissolved in ⅓ volume of distilled water with gentle stirring. A solvent such as isopropyl alcohol or acetonitrile is added in the amount of ⅔ volume and the solution is mixed. The thus prepared coating solution has a complex concentration of between 0.01 and 10 percent based upon the weight of the solution. The material to be coated is dipped in the coating solution at elevated temperatures usually ranging from 30° C. to 50° C. for about 10 minutes, followed by standing in room temperature for about 20 minutes. The coated material is taken out of the coating solution and rinsed thoroughly with distilled water or saline solution prior to drying.

EXAMPLE 2

This example demonstrates one technique for applying the coating compositions of the present invention to surfaces intended to directly contact blood.

The covalent complex (100 mg) produced according to Example 1 above is solubilized in ⅓ volume, 27 ml of distilled water with gentle stirring. Thereafter ⅔ volume, 53 ml of isopropyl alcohol or acetonitrile is added. The resulting concentration of the covalent complex in solution is about 0.125 percent by weight. The blood-contacting surface to be coated with the coating composition is dipped into the coating composition for 10 minutes at a temperature of between 30° C. to 50° C. Thereafter, the surface is allow to remain in contact with the coating composition for approximately 20 minutes, at room temperature. Thereafter, the coated surface is removed from the coating composition and rinsed thoroughly with distilled water or saline solution.

EXAMPLE 3

This example demonstrates the stability of the heparin coating compositions of the present invention on surfaces exposed to ionic environments.

Various surfaces coated according to Example 2 were evaluated for heparin activity after washing with 3 percent (by weight) sodium chloride solution. Surface heparin activity is measured in $mIU/cm^2$ according to the technique described in Sigma Diagnostics, Heparin, Procedure No. CRS 106.

Results obtained from the evaluation of heparin activity on a polycarbonate surface after washing with sodium chloride are set forth in Table 1 below.

TABLE 1

| Concentration of covalent complex in | Percent by volume of isopropyl alcohol In $IPA/H_2O$ solvent | | | | | |
|---|---|---|---|---|---|---|
| solution (% w/v) | 50 | 55 | 60 | 65 | 70 | 75 |
| 2 | 21.8 | | | | | |
| 1 | 21.6 | 24.5 | | | | |
| 0.5 | 9.9 | 23.2 | 20.7 | 23.4 | 18.0 | 5.2 |
| 0.25 | 6.8 | 8.0 | 17.6 | 16.3 | 14.7 | 14.9 |
| 0.125 | 7.1 | 10.3 | 5.4 | 13.0 | 13.1 | 11.3 |

Results obtained from the evaluation of heparin activity on a siloxane surfaces (TMCTS) after washing with sodium chloride are set forth in Table 2 below.

TABLE 2

| Concentration of covalent complex in | Percent by volume of isopropyl alcohol In $IPA/H_2O$ solvent | | | | | |
|---|---|---|---|---|---|---|
| solution (% w/v) | 50 | 55 | 60 | 65 | 70 | 75 |
| 2 | 9.0 | | | | | |
| 1 | 4.9 | | | | | |
| 0.5 | | | | | | |
| 0.25 | 0.4 | 3.8 | 3.5 | 2.0 | 1.1 | 2.4 |
| 0.125 | 4.4 | 1.6 | 2.5 | 4.8 | 1.0 | 1.9 |

Results obtained from the evaluation of heparin activity on a polyester surface after washing with sodium chloride are set forth in Table 3 below.

TABLE 3

| Concentration of covalent complex in | Percent by volume of isopropyl alcohol In $IPA/H_2O$ solvent | | | | | |
|---|---|---|---|---|---|---|
| solution (% w/v) | 50 | 55 | 60 | 65 | 70 | 75 |
| 2 | | | | | | |
| 1 | | | | | | |
| 0.5 | | | | | | |
| 0.25 | 4.5 | 4.4 | 5.5 | 3.7 | 5.3 | |
| 0.125 | 2.1 | 2.5 | 2.9 | 1.3 | 2.0 | 1.7 |

Results obtained from the evaluation of heparin activity on a polyvinyl chloride surface after washing with sodium chloride are set forth in Table 4 below.

TABLE 4

| Concentration of covalent complex in | Percent by volume of isopropyl alcohol In $IPA/H_2O$ solvent | | | | | |
|---|---|---|---|---|---|---|
| solution (% w/v) | 50 | 55 | 60 | 65 | 70 | 75 |
| 2 | | | | | | |
| 1 | | | | | | |
| 0.5 | | | | | | |

TABLE 4-continued

| Concentration of covalent complex in | Percent by volume of isopropyl alcohol In IPA/H₂O solvent | | | | | |
|---|---|---|---|---|---|---|
| solution (% w/v) | 50 | 55 | 60 | 65 | 70 | 75 |
| 0.25 | 2.6 | 2.9 | 10.0 | 6.5 | 4.0 | 2.8 |
| 0.125 | 1.8 | 2.1 | 1.0 | 2.1 | 2.1 | 2.1 |

Results obtained from the evaluation of heparin activity on a stainless steel surface after washing with sodium chloride are set forth in Table 5 below.

TABLE 5

| Concentration of covalent complex in | Percent by volume of isopropyl alcohol In IPA/H₂O solvent | | | | | |
|---|---|---|---|---|---|---|
| solution (% w/v) | 50 | 55 | 60 | 65 | 70 | 75 |
| 2 | | | | | | |
| 1 | | | | | | |
| 0.5 | | | | | | |
| 0.25 | 12.9 | 13.1 | 8.3 | 11.0 | 12.9 | 13.8 |
| 0.125 | 10.6 | 12.3 | 10.4 | 10.2 | 8.8 | 11.8 |

The combined results demonstrate that the heparin coating compositions of the present invention exhibit improved heparin activity on a wide variety of surface materials.

The foregoing is illustrative of the present invention and is not to be construed as limiting thereof. The invention is defined by the following claims, with equivalents of the claims to be included therein.

That which is claimed is:

1. A non-thrombogenic coating composition for blood-contacting surfaces, said composition comprising a covalent complex of from 1 to 30 hydrophobic silyl moieties of Formula I:

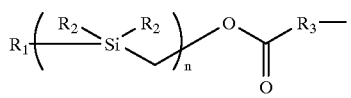

wherein
R₁ is a $C_{1-8}$ alkyl or $C_{6-32}$ aryl group,
each R₂ is independently selected from the group consisting of $C_{1-8}$ alkyl and $C_{6-32}$ aryl
R₃ is N or O, and
n is a number from 1 to 10 directly bound to sodium heparin via covalent bonding.

2. The composition according to claim 1, wherein said hydrophobic silyl moieties bind to said surfaces via hydrophobic bonding interactions.

3. The composition according to claim 1, wherein said complex comprises from 2 to 25 hydrophobic silyl moieties covalently bound to one heparin molecule.

4. The composition according to claim 1, wherein R₁ is benzyl in said hydrophobic silyl moiety of Formula I.

5. The composition according to claim 1, wherein each R₂ is an alkyl in said hydrophobic silyl moiety of Formula I.

6. The composition according to claim 1, wherein n is 2 or 3 in said hydrophobic silyl moiety of Formula I.

7. The composition according to claim 1, wherein said complex is [benzyl-bis(dimethylsilylmethyl)]-(N-heparinyl)-carbamate.

8. The composition according to claim 1, wherein said complex is [benzyl-tris(dimethylsilylmethyl)]-(N-heparinyl)-carbamate.

9. A non-thrombogenic medical device comprising surfaces for contacting blood, said surfaces having coated thereon a non-thrombogenic coating composition comprising a covalent complex of from 1 to 30 hydrophobic silyl moieties of Formula I:

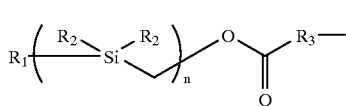

wherein
R₁ is a $C_{1-8}$ alkyl or $C_{6-32}$ aryl group,
each R₂ is independently selected from the group consisting of $C_{1-8}$ alkyl and $C_{6-32}$ aryl,
R₃ is N or O, and
n is a number from 1 to 10 directly bound to heparin via covalent bonding.

10. The device according to claim 9, wherein said hydrophobic silyl moieties bind to said surfaces via hydrophobic bonding interactions.

11. The device according to claim 9, wherein said complex comprises from 2 to 25 hydrophobic silyl moieties covalently bound to one heparin molecule.

12. The device according to claim 9, wherein R₁ is benzyl in said hydrophobic silyl moiety of Formula I.

13. The device according to claim 9, wherein each R₂ is an alkyl in said hydrophobic silyl moiety of Formula I.

14. The device according to claim 9, wherein n is 2 or 3 in said hydrophobic silyl moiety of Formula I.

15. The device according to claim 9, wherein said complex is [benzyl-bis(dimethylsilylmethyl)]-(N-heparinyl)-carbamate.

16. The device according to claim 9, wherein said complex is [benzyl-tris(dimethylsilylmethyl)]-(N-heparinyl)-carbamate.

17. The device according to claim 9, wherein said device is selected from the group consisting of oxygenators, oxygenator circuits, heart-lung bypass circuits, blood gas exchange devices, blood filters, artificial blood vessels, artificial valves, prosthetics, stents, catheters, heat exchangers, and hypodermic needles.

18. A method for rendering blood-contacting surfaces of a medical device non-thrombogenic, said method comprising coating said surfaces with a non-thrombogenic coating composition comprising a covalent complex of from 1 to 30 hydrophobic silyl moieties of Formula I:

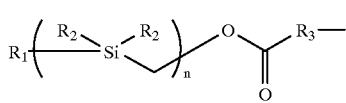

wherein
R₁ is a $C_{1-8}$ alkyl or $C_{6-32}$ aryl group,
each R₂ is independently selected from the group consisting of $C_{1-8}$ alkyl and $C_{6-32}$ aryl,
R₃ is N or O, and
n is a number from 1 to 10 directly bound to heparin via covalent bonding.

19. The method according to claim 18, wherein said hydrophobic silyl moieties bind to said surfaces via hydrophobic bonding interactions.

20. The method according to claim 18, wherein said complex comprises from 2 to 25 hydrophobic silyl moieties covalently bound to one heparin molecule.

21. The method according to claim 18, wherein $R_1$ is benzyl in said hydrophobic silyl moiety of Formula I.

22. The method according to claim 18, wherein each $R_2$ is an alkyl in said hydrophobic silyl moiety of Formula I.

23. The method according to claim 18, wherein n is 2 or 3 in said hydrophobic silyl moiety of Formula I.

24. The method according to claim 18, wherein said complex is [benzyl-bis(dimethylsilylmethyl)]-(N-heparinyl)-carbamate.

25. The method according to claim 18, wherein said complex is [benzyl-tris(dimethylsilylmethyl)]-(N-heparinyl)-carbamate.

26. The method according to claim 18, which further comprises the step of solubilizing said complex in a solvent prior to said step of coating said surface.

27. The method according to claim 18, wherein said step of coating said surface comprises dipping said surface into said coating composition comprising said complex.

28. The method according to claim 18, wherein said step of coating said surface comprises pumping said coating composition comprising said complex onto said surface.

* * * * *